United States Patent
Nagao et al.

(10) Patent No.: US 7,944,207 B2
(45) Date of Patent: May 17, 2011

(54) MAGNETIC RESONANCE IMAGING APPARATUS AND METHOD

(75) Inventors: Hisako Nagao, Tokyo (JP); Takayuki Abe, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 739 days.

(21) Appl. No.: 11/917,129

(22) PCT Filed: Jun. 14, 2006

(86) PCT No.: PCT/JP2006/311905
§ 371 (c)(1),
(2), (4) Date: Dec. 10, 2007

(87) PCT Pub. No.: WO2006/134958
PCT Pub. Date: Dec. 21, 2006

(65) Prior Publication Data
US 2010/0213937 A1    Aug. 26, 2010

(30) Foreign Application Priority Data
Jun. 14, 2005  (JP) .................................. 2005-173948

(51) Int. Cl.
*G01V 3/00* (2006.01)
(52) U.S. Cl. .......................... 324/309; 324/307; 600/410
(58) Field of Classification Search .................. 324/309, 324/307; 600/410
See application file for complete search history.

(56) References Cited

U.S. PATENT DOCUMENTS

| 6,301,497 | B1 * | 10/2001 | Neustadter ..................... 600/410 |
| 7,756,566 | B2 * | 7/2010 | Machida ........................ 600/415 |
| 2001/0009369 | A1 | 7/2001 | Shimo et al. |
| 2009/0309595 | A1 * | 12/2009 | Yatsui ............................. 324/309 |
| 2010/0106002 | A1 * | 4/2010 | Sugiyama et al. ............. 600/410 |

FOREIGN PATENT DOCUMENTS

| JP | 2000-287941 | 10/2000 |
| JP | 2001-78979 | 3/2001 |
| JP | 2001-198100 | 7/2001 |
| JP | 2003-190102 | 7/2003 |

* cited by examiner

Primary Examiner — Louis M Arana
(74) Attorney, Agent, or Firm — Cooper & Dunham LLP (57) ABSTRACT

A magnetic resonance imaging apparatus is configured to divide an object to be examined into a plurality of regions in a predetermined direction, set images of slice positions for each of the regions so that the slice positions are continuous in each region, obtain an image of each of the regions while moving the object stepwise, and acquire a plurality of image data having three types of categories for the region, the slice position and the imaging sequence. The magnetic resonance imaging apparatus selectively sets one of the three types of categories and rearranges and displays a plurality of images having the set category in the lengthwise direction or the lateral direction according to the two other categories that have not been selectively set.

20 Claims, 9 Drawing Sheets

MAGNETIC RESONANCE IMAGING APPARATUS AND METHOD

TECHNICAL FIELD

The present invention relates to a magnetic resonance imaging (hereinafter referred to as MRI) apparatus and method, particularly to a technique for appropriately displaying an image acquired by multi-station/multi-slice imaging method (hereinafter referred to as multi-station/multi-slice MRI).

BACKGROUND ART

In MRI field, a technique is commonly known for imaging a wide range or the whole body of an object to be examined while laying the object on the table and moving the table stepwise in the gantry of the MRI apparatus. Such technique is referred to as a multi-station MRI, and is for imaging a wide range or the whole body of the object while moving the table, for example, after setting a slice surface of an image parallel to the surface of the table (for example, refer to Patent Document 1).

Patent Document 1: U.S. Pat. No. 6,311,085

Meanwhile, in multi-station MRI, the number of slices (the number of slices in vertical direction to the table surface on which the object is laid) does not have to be one, and may be multi-sliced.

In such case, the inventors of the present invention took notice of the following problem. That is, in multi-station/multi-slice MRI, there are cases that the imaging takes place using a plurality of imaging sequences to further obtain multilateral diagnostic images of the object. In this case, while many images can be obtained by imaging the whole body of the object by multi-station/multi-slice using a plurality of imaging sequences, it is hard for an observer to comprehend as to which imaging sequence of which position each image belong to due to large number of images arranged on the monitor, unless these images are properly displayed.

BRIEF SUMMARY

In an aspect of this disclosure, there are provided an MRI apparatus and method capable of properly displaying the images obtained by combining the multi-station/multi-slice MRI and a plurality of imaging sequences.

In another aspect, there is provided an MRI apparatus comprising:

imaging means for dividing an object into a plurality of regions in a predetermined direction, setting images of a plurality of slice positions for each of the plurality of regions so that each of the slice positions of the respective regions are continuous, and imaging each of the regions while moving the object stepwise in a plurality of sequences; and display means for acquiring a plurality of image data having three types of categories: the region, the slice position and the imaging sequence by the imaging means, and displaying the image data, is characterized in comprising:

selecting means for selecting one of the three types of categories; and rearrangement display means for arranging and displaying the image data of the category selected by the selecting means according to the two other categories which have not been selected in the longitudinal direction or the lateral direction on the display means.

In another aspect of this disclosure, there is provided an MRI method comprising:

(1) a step for generating the plurality of image data having three types of categories: the region, slice position and imaging sequence, by imaging the respective regions of an objective to be examined in a plurality of slices and a plurality of imaging sequences while moving a table stepwise on which the object is laid, is characterized in comprising:

(2) a step for selecting as to which category of the three types of categories the display of the plurality of image data should be based on;

(3) a step for rearranging the plurality of image data according to the other categories which have not been selected;

(4) a step for displaying the rearranged plurality of image data; and (5) a step for switching the plurality of image data display within the category selected in the step (2).

BRIEF DESCRIPTION OF THE DIAGRAMS

BEST MODE FOR CARRYING OUT THE INVENTION

Figure 1:
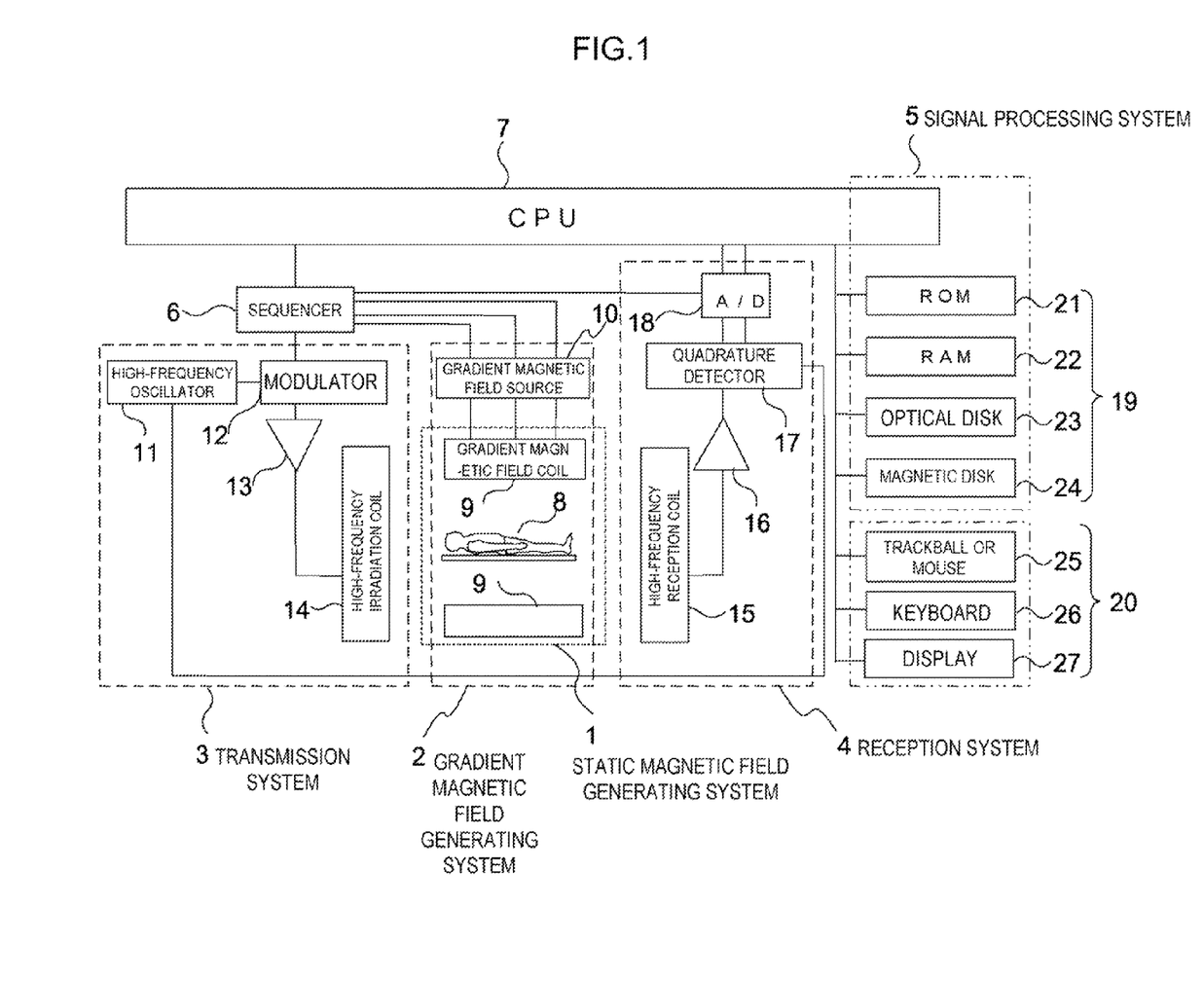
FIG. 1 is a block diagram of the general configuration of the MRI apparatus related to the present invention.

FIG. 1 is a block diagram showing the general configuration of the MRI apparatus related to the present invention. As shown in FIG. 1, this MRI apparatus mainly comprises static magnetic field generating system 1, gradient magnetic field generating system 2, transmission system 3, reception system 4, signal processing system 5, control system (sequencer) 6 and CPU 7.

Static magnetic field generating system 1 is for generating uniform static magnetic field in a space around object 8 (imaging space), and formed by magnetic devices using a method such as permanent magnet method, normal conduction or superconduction method.

Gradient magnetic field generating system 2, when, for example, the direction of static magnetic field is set as Z-direction and the two directions that are orthogonal to the Z-direction are set as X and Y-directions, is formed by three gradient magnetic field coils 9 for generating gradient magnetic field pulses in these three-axes directions and gradient magnetic field sources 10 for driving threes coils respectively. By driving gradient magnetic field sources 10, gradient magnetic field pulses can be generated in the direction of three axes x, y and Z or the direction by which these three directions are synthesized. The gradient magnetic field pulses are applied for imparting the positional information to NMR signals generated from object 8.

Transmission system 3 consists of high-frequency oscillator 11, modulator 12, high-frequency amplifier 13 and high-frequency irradiation coil 14 for transmission. Electromagnetic waves (high-frequency signals, RF pulses) for generating magnetic resonance in atomic nuclei of atomic element by which the object is formed are irradiated, by amplifying RF pulses generated by high-frequency oscillator 11 in high-frequency amplifier 13 and applying them to high-frequency irradiating coil 14 after modulating the RF pulses into predetermined envelop signals in modulator 12. High-frequency irradiating coil 14 is usually placed in the vicinity of the object.

Reception system 14 consists of high-frequency reception coil 15, amplifier 16, quadrature detector 17 and A/D converter 18. NMR signals generated from the object as response to the RF pulses irradiated from high-frequency irradiation coil 14 for transmission are converted into digital quantity by A/D converter 18 via quadrature detector 17 after detected by high-frequency reception coil 15 for reception and amplified by amplifier 16, and transmitted to signal processing system 5 as two groups of collected data.

Signal processing system 5 consists of CPU 7, storage device 19 and operation unit 20, and performs in CPU 7 a variety of signal processing (such as Fourier transformation, calculation of correction coefficient and image Reconstruction) to the digital signals received by reception system 4. Storage device 19 comprises devices such as ROM 21, RAM 22, optical disk 23 and magnetic disk 24, and is for storing, for example, programs for performing image analysis and measurement over time or invariable parameters to use for the execution of the programs in ROM 21, measurement parameters acquired in the entire measurement or echo signals, etc, detected in the reception system in RAM 22, and the reconstructed image data in optical disk 23 or magnetic disk 24. Operation unit 20 comprises input means such as a trackball or mouse 25 and keyboard 26, and display 28 for displaying a GUI (graphical user interface) for input and for displaying the result of processing, etc., in signal processing system 5. Information for each process and control performed by CPU 7 are inputted via operation 20. Also, the images obtained by the imaging process are displayed on display 27.

Embodiment 1

Figure 2:
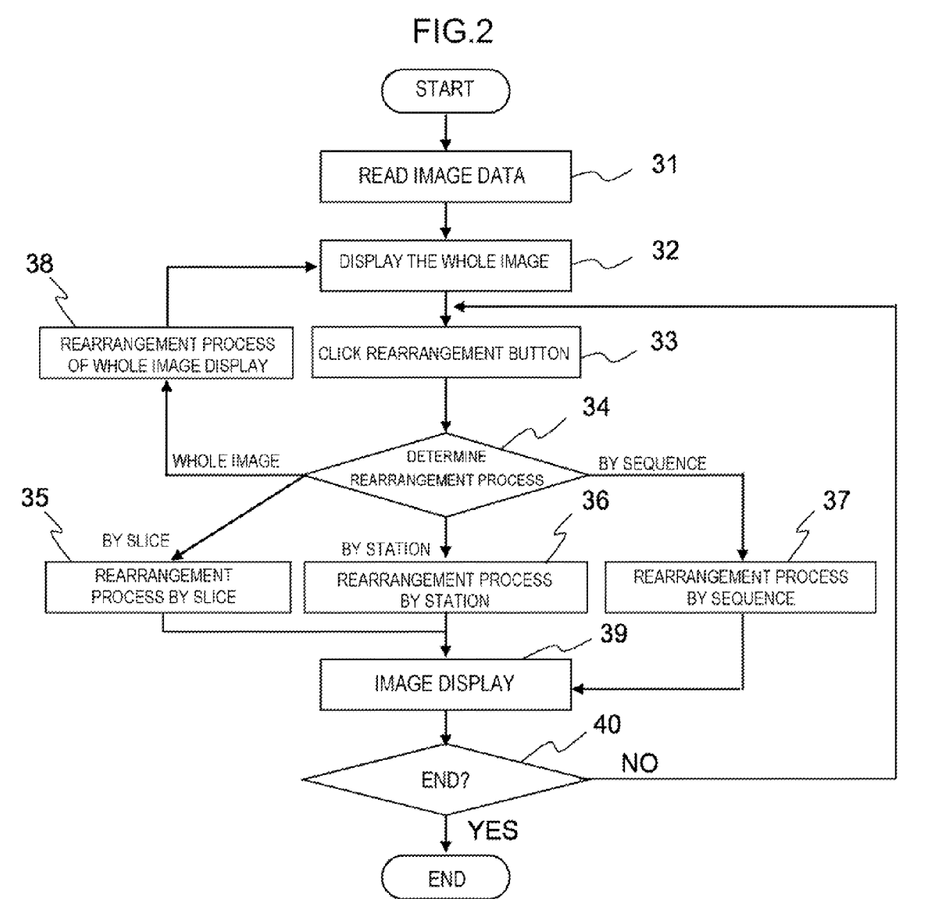
FIG. 2 is a flow chart showing a step of display process by rearranging the images in the MRI apparatus related to embodiment 1 of the present invention.

Next, embodiment 1 of the present invention will be described using FIG. 2. FIG. 2 is a flow chart illustrating the steps for display process by rearranging the images, in the MRI apparatus related to embodiment 1 of the present invention. In this regard, however, that the multi-station/multi-slice imaging is performed using a plurality of imaging sequences as a preparative of the step for display process by rearranging the images in FIG. 2, and the imaging result thereof is stored in optical disk 23 or magnetic disk 24 as image data.

Figure 3:
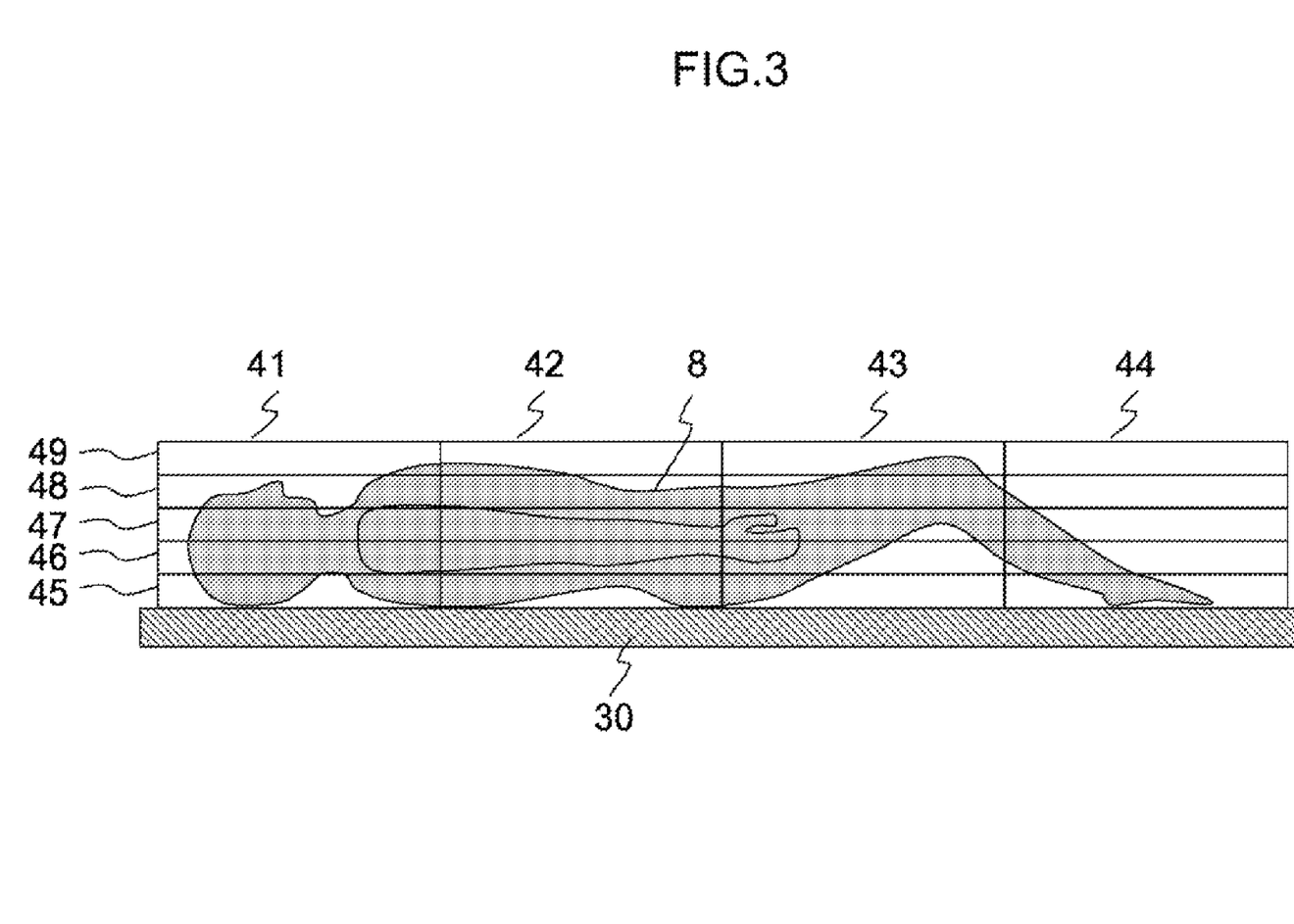
FIG. 3 illustrates the multi-station imaging in multi-slice.

Here, multi-station/multi-slice imaging means the case that object 8 laid on table 30 is segmentilized into four sections in lateral direction (body-axis direction) on the diagram then setting those sections as four stations 41, 42, 43 and 44, and also into five sections in lengthwise direction (body-thickness direction) on the diagram, then imaging each station by five slices 45, 46, 47, 48 and 49, as shown in FIG. 3. In this case, the slices set for each station share the same planes for all the stations.

Also, the case for performing a plurality of imaging methods can be a case, of combining, for example, the case for imaging T1-weighted image, T2-weighted image and STIR image for a metasearch of a metastatic tumor for diagnosis, and the case for imaging T2-weighted image and DWI image for determining the grade of malignancy of the tumor. Hereinafter, the respective steps of the flow chart in FIG. 2 will be described in order.

(Step 31)

All of the image data obtained by a plurality of imaging methods in the previous step is read in CPU 7 from optional disk 23.

(Step 32)

Figure 4:
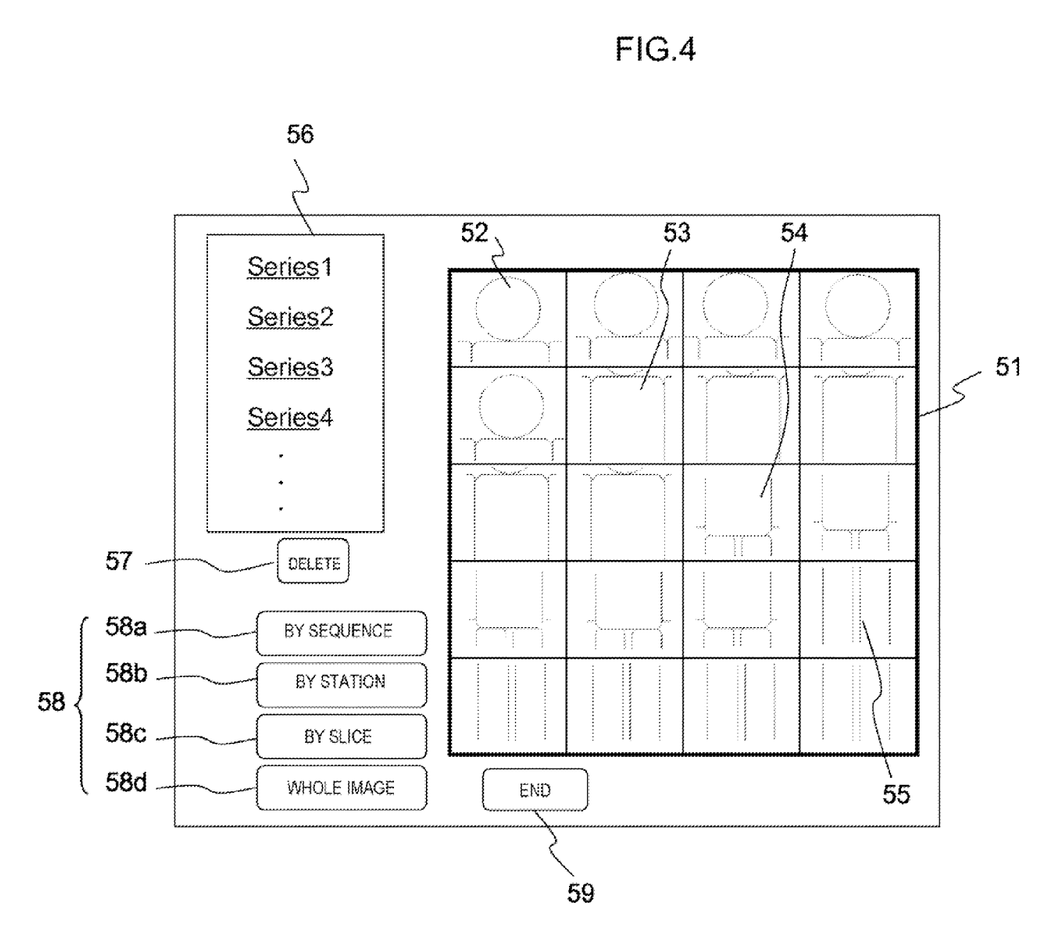
FIG. 4 is an example of the whole image display.

The image read in step 31 is displayed by a whole image display. The whole image display is a display method to display the obtained images in order from the upper left to the lower right on display 27. The display example of the whole image display is shown in FIG. 4. In FIG. 4, 51 is the image display part on the display screen, wherein the head images of the object are sequentially displayed for the portion of 5 slices from the upper left (52) to the right, next the chest images of the object are sequentially displayed for the portion of 5 slices from the second row from the left on the second line (53), next the abdominal images of the object are sequentially displayed for the portion on 5 slices from the third row from the left on the third line (54), and the leg images of the object are sequentially displayed for the portion of 5 slices from the far right of the fourth line (55). 56 is an index display column for the case of collecting up the image data loaded in step 32 as series by dividing them into several groups. In FIG. 4, the image data are divided into several groups by "series 1, 2, 3, 4 . . . ", and the operator can click on the desired series of indexes and display the target image data group on image display 51. Also, 57 is a delete button, and is for deleting unnecessary information from image data of the whole image display loaded in step 32 by clicking the image to be deleted and delete button 57.

Further, 58 is a button for the operator to input as to which method should be ordered to use for the alignment of the images in step 33, and consists of, from the top in order, display button by sequences 58a, display button by stations 58b, display button by slices 58c and whole image display button 58d.

(Step 33)

In the present step, the operator inputs the information as to which method to be used for the rearrangement of the images, and the command for starting the rearrangement process is transmitted. In concrete terms, 58 in FIG. 4 is used for selecting as to which rearrangement process should be performed, and one of the selected buttons 58a-58d is clicked.

(Step 34)

In the present step, determination is made by as to which arrangement process is to be commanded for performing in step 33 by CPU 7. Then the process is performed to proceed with steps 35~37 depending on which arrangement process is to be carried out.

(Step 35)

In the present step, the rearrangement process of the image data by slice is executed. When the rearrangement process is ended, step 39 is to proceed and the image data by slice is displayed.

(Step 36)

In the present step, rearrangement process of the image data by station is carried out. When the rearrangement process is ended, step 39 is to proceed and the image data by station are displayed.

(Step 37)

In the present step, rearrangement process of the image data by sequence is carried out. When the rearrangement process is ended, step 39 is to proceed and the image data by sequence are displayed.
(Step 38)

In the present step, rearrangement process for a whole image display is carried out. When the rearrangement process is ended, step 32 is to proceed and the whole image data is displayed.
(Step 39)

Figure 5:
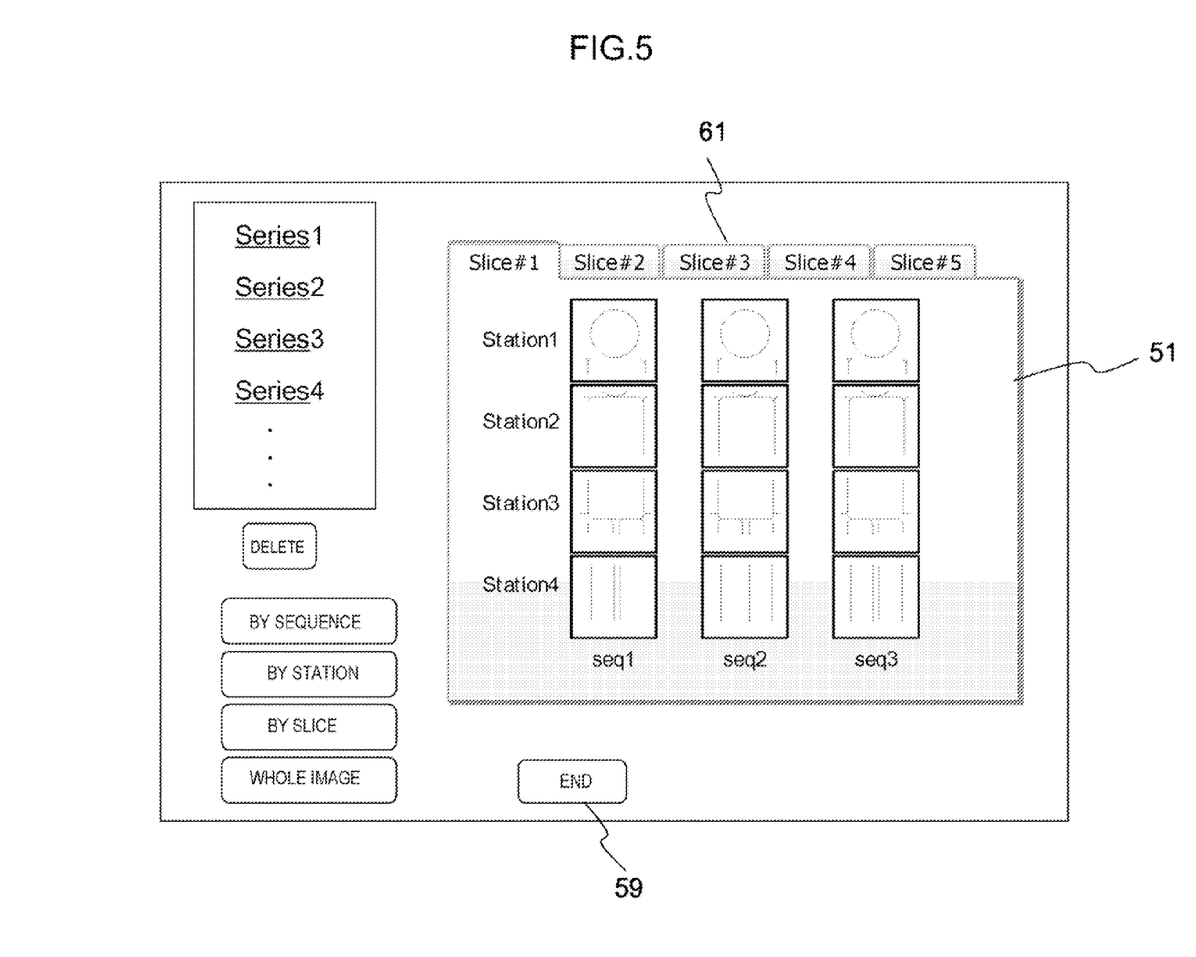
FIG. 5 is a display example of the result from rearrangement of image data by slice.

In the present step, the images are displayed in accordance with the rearrangement process of the respective steps 35~37. First, FIG. 5 is a display example of the result from rearrangement of the images by slice performed in step 35. In FIG. 5, 61 are the tabs for switching the images (pages) upon determining which slice number of image data by slice should be displayed on display unit 51, and is capable of switching the page of images to be displayed by selecting the first slice, second slice, third slice, fourth slice or fifth slice of the pages from the left. Then in each displayed page in the category of slice, the first~fourth images by station are arranged lengthwise, and the first~third images by sequence (imaging method) are arranged crosswise to be displayed respectively. In FIG. 5, slice #1 is selected, and the images by combination of station (41)~station (44) are displayed in lengthwise and sequence 1~sequence 3 are displayed in crosswise.

Figure 6:
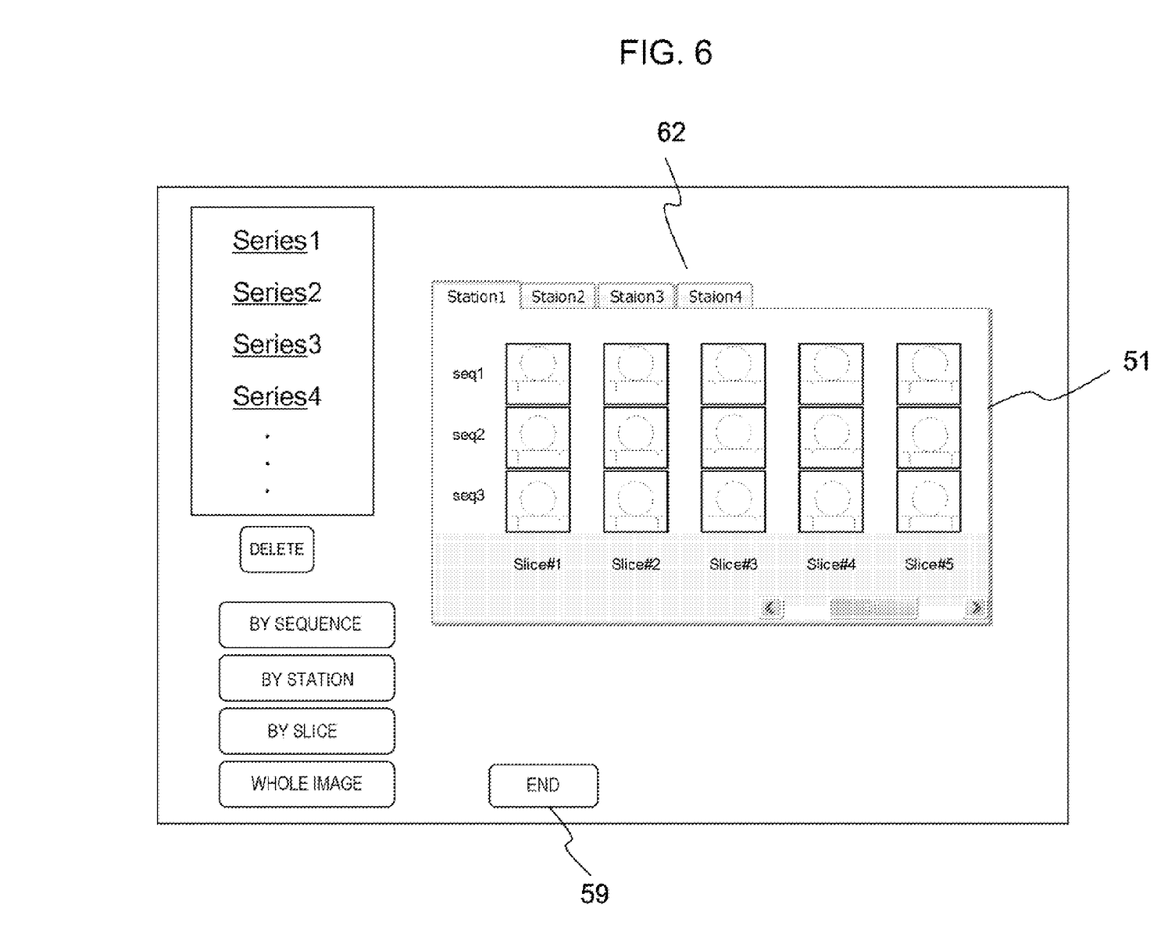
FIG. 6 is a display example of the result from rearrangement of image data by station.

Next, FIG. 6 is a display example of the result from the rearrangement of the images by station carried out in step 36. In FIG. 6, 62 are the tabs for switching the images (pages) of image data by station to be displayed on display unit 51, and is capable of switching the page of images to be displayed by selecting the first station, second station, third station and fourth station of the pages from the left. Then in each displayed page of the station, the first~third images by sequence (imaging method) are arranged lengthwise, and the first~fifth images by slices are arranged crosswise respectively. In FIG. 6, station (41) is selected, and images of sequence 1~sequence 3 are displayed by groups for each slice number.

Figure 7:
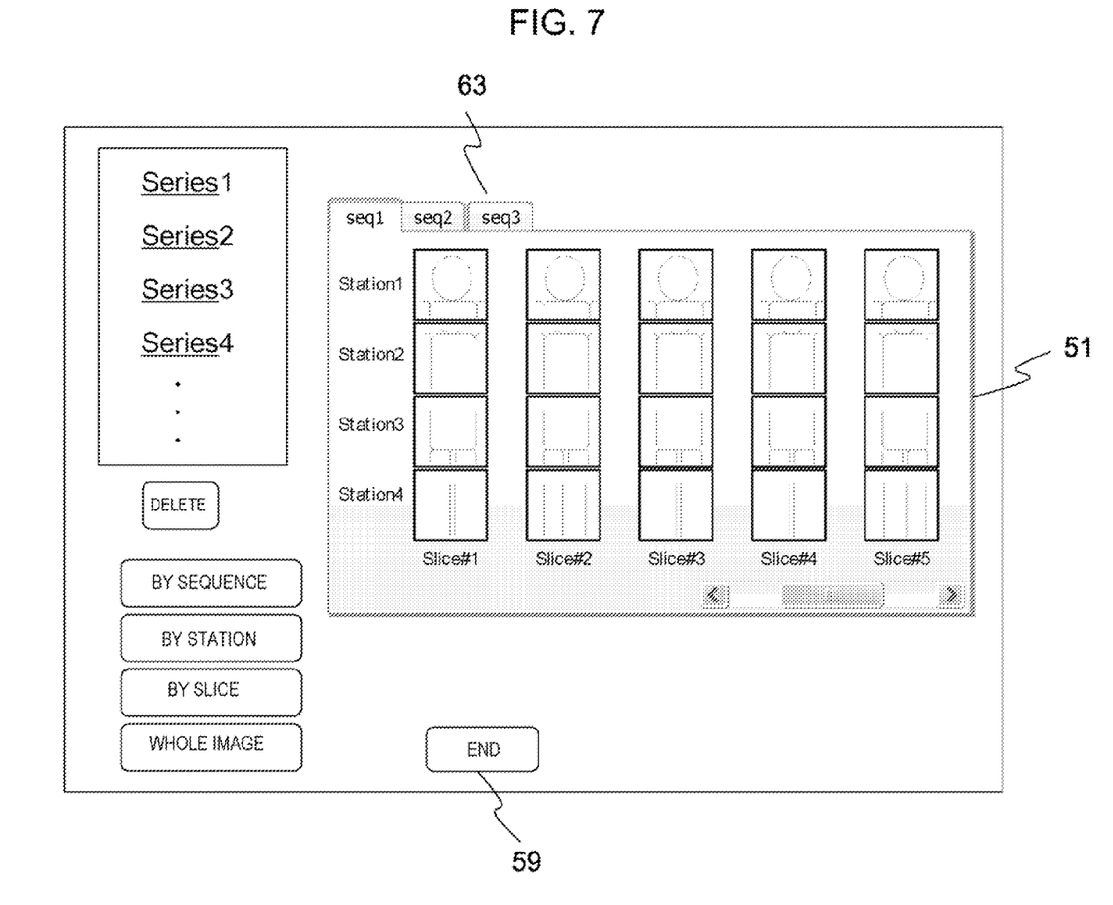
FIG. 7 is a display example of the result from rearrangement of image data by sequence (imaging method).

Next, FIG. 7 is a display example of the result from the rearrangement of the image data by sequence (imaging method) in step 37. In FIG. 7, 63 are the tabs for switching the displayed page of image data by sequence (imaging method) to be displayed on display unit 51, and is capable of switching the page of images to be displayed by selecting the first sequence, second sequence and third sequence of the pages from the left. Then in each page of the station, the first~fourth images by station are arranged lengthwise, and the first~fifth images by slice are arranged crosswise respectively. In FIG. 7 sequence 1 is selected, and images of station 1~station 4 are displayed by groups for each slice 1~slice 5. Meanwhile, display format of the screen illustrated in FIG. 5, FIG. 6 and FIG. 7 and a software for switching the images are programmed in advance, and installed in an optical disk or magnetic disk 24.
(Step 40)

Determination is made whether to end the process by the present embodiment for displaying by rearranging the images. When the process is ended, ending button 59 is clicked. When it is determined not to end the process, step 33 is to proceed again. In accordance with the above-described embodiment, in multi-station/multi-slice MRI, it is possible to display the images obtained by a plurality of imaging methods appropriately. To be more precise, the present embodiment comprises means for selecting one category from the categories of a slice number, station number and sequence, arranging the images of the two other categories two-dimensionally, and switching the display screens within the selected category. By comprising this means, it is easier for the operator (or an image observer) to comprehend as to which category of the three categories the images displayed belong to.

Embodiment 2

Figure 8:
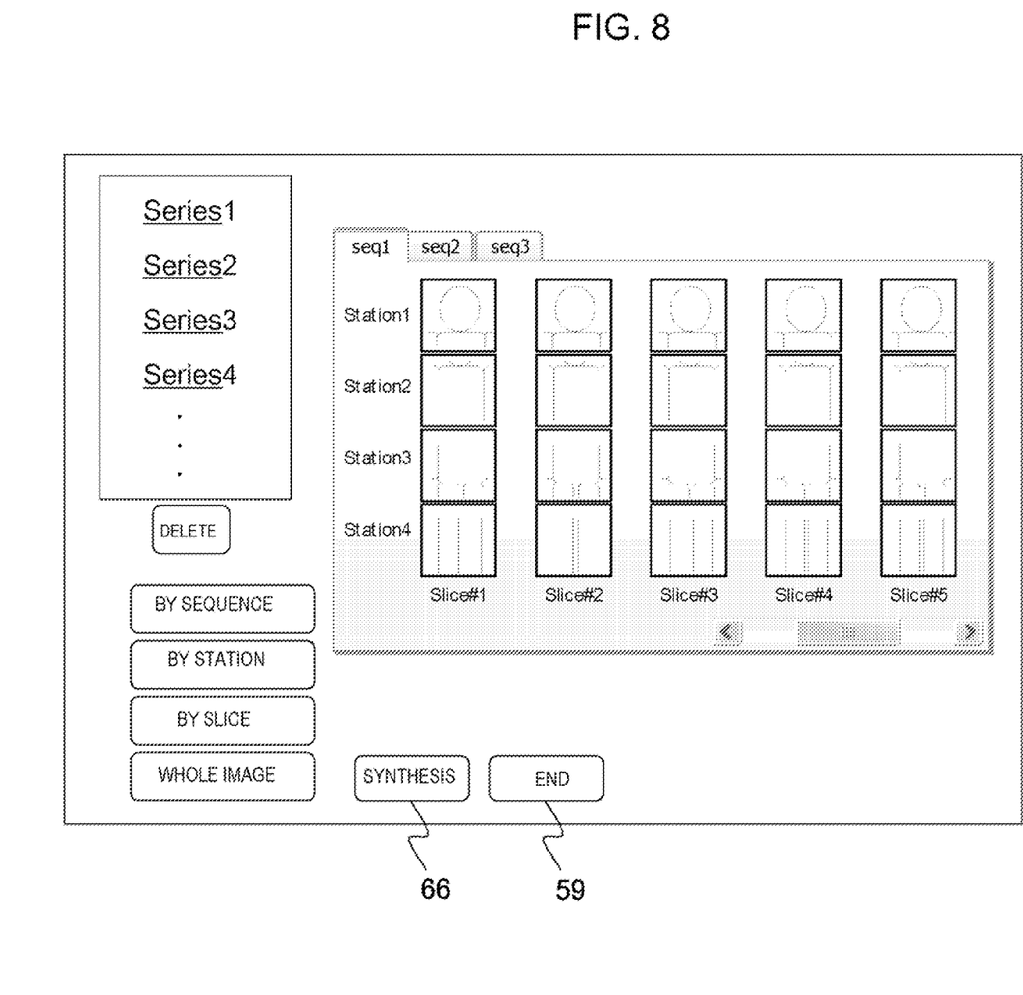
FIG. 8 shows a display example of a rearrangement of the image data by sequence, with a synthesis button at the lower side of the screen.
Figure 9:
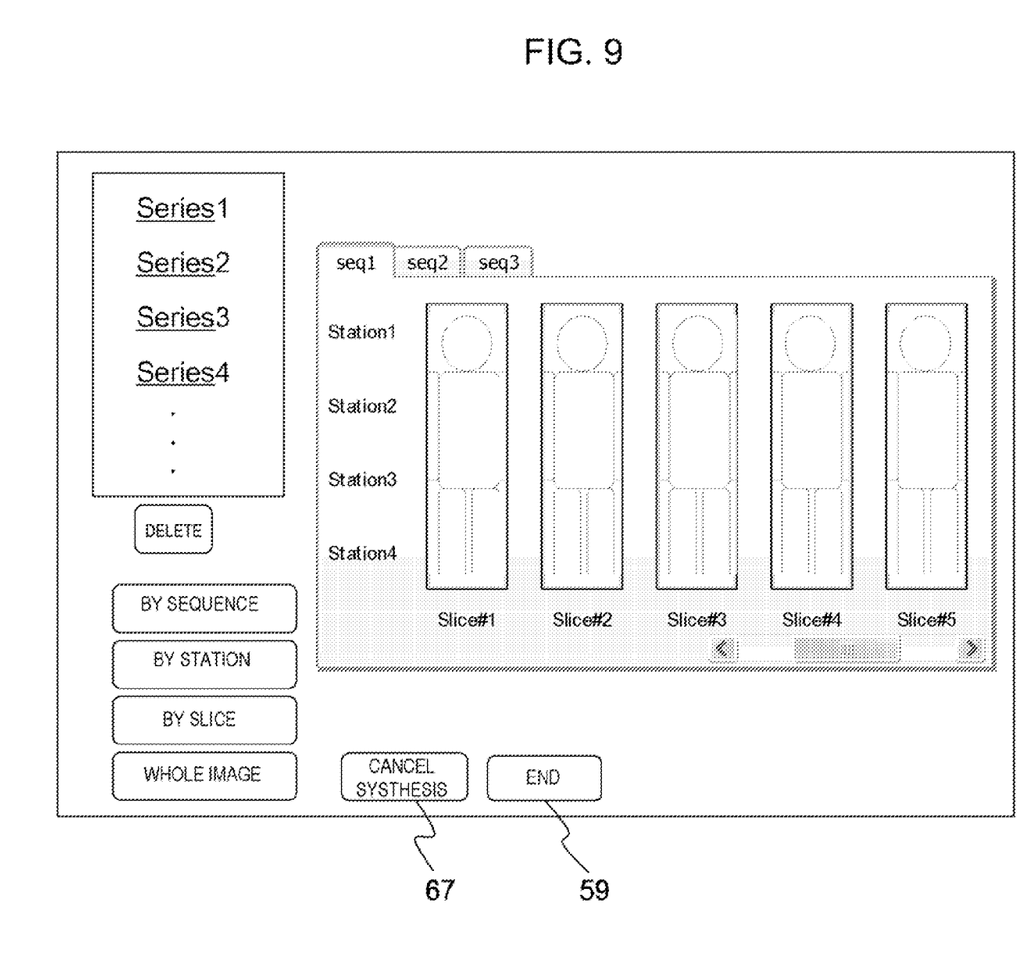
FIG. 9 shows a result of a synthesis process carried out by clicking the synthesis button.

Next, embodiment 2 of the present invention will be described using FIG. 8 and FIG. 9. FIG. 8 is a display example of the rearranged image data by sequence (imaging method) as with FIG. 7, but synthesis button 66 is displayed on the lower portion of the screen. This synthesis button is for performing image composition to make a number of images look like one image, by connecting the images for each station that are arranged lengthwise. FIG. 9 is a result of image composition performed by clicking synthesis button 66. It is set so that when synthesis button 66 is once clicked, the display of the button changes to (67) for canceling the synthesis. By implementing the image composition, the strain is corrected so that the mutual borderlines of the respective images turn out to make a continuous image, whereby displaying the image as a whole body and facilitating the observation of the image. The synthesis process in the present embodiment can be applied not only to the case of displaying the image data by arranging them by sequence (imaging method) as shown in FIG. 7, but also to the case of rearranging the image data by slice as shown in FIG. 5.

The present invention is not to be taken by way of limitation, and various changes may be made without departing from the scope of the invention. For example, in the display pattern of the above-mentioned FIG. 5~FIG. 7, a function may be provided for switching the alignment category of lengthwise direction and lateral direction. For example, in FIG. 5, it goes without saying that a function may be provided for switching the arrangement so that the kinds of sequence are arranged in lengthwise direction and the images of the respective stations are arranged in lateral direction in order.

The invention claimed is:
1. An magnetic resonance imaging apparatus comprising:
a control part configured to divide an object to be examined into a plurality of regions in a predetermined direction, set images of a plurality of slice positions for each of the plurality of regions so that the respective slice positions of the respective regions are continuous to each other, and cause to be imaged each of the regions by a plurality of sequences while the object is moved stepwise; and
an operation part configured to acquire a plurality of image data organizable according to any of three types of categories of according-to-region, according-to-slice-position and according-to-imaging-sequence, the operation part including a display part configured to display images based on the acquired image data,
wherein the control part selects one of the three types of categories, causes the images to be organized in accordance with the selected type of categories, rearranges the image data in lengthwise direction or lateral direction on the display part in accordance with the two other types of categories which have not been selected, and causes the rearranged image data to be displayed.

2. The magnetic resonance imaging apparatus according to claim 1, wherein the operation part further includes a user interface including one or more buttons, the selection of the one type from the three types of categories is performed in response to a button of the user interface being clicked.

3. The magnetic resonance imaging apparatus according to claim 1, wherein the operation part further includes a user interface, and the rearrangement of the image data by the control part is performed in response to clicking of a tab provided in the user interface.

4. The magnetic resonance imaging apparatus according to claim 1, wherein a plurality of images arranged two-dimensionally based on the rearranged image data are provided on the display part by arranging the images in the lengthwise direction in accordance with one of the two types of categories which have not been selected by the control part, and arranging the images in the lateral direction in accordance with the other type of the two types of categories which have not been selected by the control part.

5. The magnetic resonance imaging apparatus according to claim 1, wherein the operation part further includes a user interface, and when the type of categories of according-to-region is selected in response to user operation through the user interface, the image data is rearranged in the lengthwise direction or the lateral direction, in accordance with one of according-to-slice-position and according-to-imaging-sequence.

6. The magnetic resonance imaging apparatus according to claim 1, wherein the operation part further includes a user interface, and when the type of categories of according-to-slice-position is selected in response to user operation through the user interface, the image data is rearranged in the lengthwise direction or the lateral direction, in accordance with one of according-to-region and according-to-imaging-sequence.

7. The magnetic resonance imaging apparatus according to claim 1, wherein the operation part further includes a user interface, and when the type of categories of according-to-imaging-sequence is selected in response to user operation through the user interface, the image data is rearranged in the lengthwise direction or the lateral direction, in accordance with one of according-to-region and according-to-slice-position.

8. The magnetic resonance imaging apparatus according to claim 1, wherein the operation part further includes a user interface, and in a case that the type of categories of according-to-slice-position or according-to-imaging-sequence is selected in response to user operation through the user interface, the control part causes a whole body image of the object to be displayed by connecting a plurality of the images arranged next to each other.

9. The magnetic resonance imaging apparatus according to claim 1, wherein the control part is further configured to switch the arrangement of the image data in the lengthwise direction and the arrangement of the image data in the lateral direction.

10. The magnetic resonance imaging apparatus according to claim 1, further comprising moving means for moving the object while performing an imaging.

11. An magnetic resonance imaging method, comprising:
(1) a step for imaging regions of an object to be examined in a plurality of respective slices and a plurality of respective stations while moving a table stepwise on which the object is laid, and generating a plurality of image data organizable according to any of three types of categories of according-to-region, according-to-slice-position and according-to-imaging-sequence;
(2) a step for selecting, as a basis for organizing the plurality of image data, one type of the three types of categories;
(3) a step for rearranging the image data to be displayed in lengthwise direction or lateral direction according to the other types of categories which have not been selected;
(4) a step for displaying the rearranged plurality of image data; and
(5) a step for switching the display of the plurality of image data in the step (4) within the type of categories selected in the step (2).

12. The magnetic resonance imaging method according to claim 11, wherein the display of image data in the step (4) is performed by two-dimensionally arranging the images in the lengthwise direction or the lateral direction in accordance with the two categories which have not been selected in step (2), and the method further comprises:
(6) a step for switching the display of the categories in the lengthwise direction and the lateral direction of the two-dimensionally rearranged image data.

13. The magnetic resonance imaging method according to claim 11, further comprising:
(7) a step for displaying a whole body image of the object by connecting the adjacently arranged image data, when the type of categories of according-to-slice-position or according-to-imaging-sequence is selected in (2).

14. The magnetic resonance imaging method according to claim 11, further comprising:
(8) a step for displaying the plurality of image data obtained in the step (1) as a whole image display in order of the type of categories selected in (2).

15. The magnetic resonance imaging method according to claim 14, further comprising:
(9) a step for deleting a display of arbitrary image data from the whole image display.

16. The magnetic resonance imaging method according to claim 11, wherein the selection of the one type from the three types of categories in the step (2) is performed in response to clicking of a button in a user interface of a magnetic resonance imaging apparatus.

17. The magnetic resonance imaging method according to claim 11, wherein the switching of the display in the step (5) is performed in response to clicking of a tab provided in a user interface of the magnetic resonance imaging apparatus.

18. The magnetic resonance imaging method according to claim 11, wherein when the type of categories of according-to-region is selected in the step (2) in response to user operation through a user interface of a magnetic resonance imaging apparatus, the image data is rearranged in the lengthwise direction or the lateral direction, in accordance with one of according-to-slice-position and according-to-imaging-sequence.

19. The magnetic resonance imaging method according to claim 11, wherein when the type of categories of according-to-slice-position is selected in the step (2) in response to user operation through a user interface of a magnetic resonance imaging apparatus, the image data is rearranged in the lengthwise direction or the lateral direction, in accordance with one of according-to-region and according-to-imaging-sequence.

20. The magnetic resonance imaging method according to claim 11, wherein when the type of categories of according-to-imaging-sequence is selected in the step (2) in response to user operation through a user interface of a magnetic resonance imaging apparatus, the image data is rearranged in the lengthwise direction or the lateral direction, in accordance with one of according-to-region and according-to-slice-position.

* * * * *